United States Patent [19]

Morris et al.

[11] Patent Number: 5,041,621

[45] Date of Patent: Aug. 20, 1991

[54] PROCESS FOR THE PREPARATION OF DIHYDROXY ESTERS

[75] Inventors: Don L. Morris; Gary C. Luce, both of Longview, Tex.

[73] Assignee: Eastman Kodak Company, Rochester, N.Y.

[21] Appl. No.: 413,355

[22] Filed: Sep. 27, 1989

[51] Int. Cl.$^5$ .............................. C07C 69/66
[52] U.S. Cl. .................................... 560/189
[58] Field of Search ........................ 170/189

[56] References Cited

U.S. PATENT DOCUMENTS

| | | | |
|---|---|---|---|
| 3,047,618 | 7/1962 | Selwitz et al. | 260/494 |
| 3,641,117 | 2/1972 | Platz et al. | 260/484 |
| 3,641,118 | 2/1972 | Platz et al. | 260/484 |
| 3,696,005 | 10/1972 | Tucks et al. | 203/35 |
| 3,709,923 | 1/1973 | Stapp | 260/468 |
| 3,729,506 | 4/1973 | Merger et al. | 260/484 |
| 3,778,465 | 12/1973 | Barnstorf | 560/189 |
| 3,852,335 | 12/1974 | Merger et al. | 260/484 |
| 3,862,215 | 1/1975 | Merger et al. | 260/484 |
| 4,074,062 | 2/1978 | Murakami et al. | 560/189 |
| 4,082,788 | 4/1978 | Mims . | |
| 4,225,726 | 9/1980 | Morris et al. | 560/238 |
| 4,398,034 | 8/1983 | Edmonson et al. | 560/1 |
| 4,665,219 | 5/1987 | Merger et al. | 560/189 |
| 4,762,947 | 8/1988 | Niaomlya et al. | 560/189 |

FOREIGN PATENT DOCUMENTS 705843 7/1931 France .

OTHER PUBLICATIONS

Journal of the American Chemical Society, vol. 74, pp. 5133–5135 (1952).

*Primary Examiner*—Paul J. Killos
*Attorney, Agent, or Firm*—Mark A. Montgomery; William P. Heath, Jr.

[57] ABSTRACT

Process is disclosed for the preparation of dihydroxy esters such as hydroxypivalyl hydroxypivalate from hydroxy aldehydes such as hydroxypivaldehyde by contacting said hydroxy aldehydes with low levels of at least one elemental metal selected from a defined group of metals. Reaction product is readily recovered without the need for extensive catalysts neutralization and/or removal procedures.

12 Claims, No Drawings

PROCESS FOR THE PREPARATION OF DIHYDROXY ESTERS

DESCRIPTION

This invention relates to the conversion of hydroxy aldehydes to produce dihydroxy esters.

BACKGROUND OF THE INVENTION

The use of magnesium-containing compounds to catalyze the dimerization of hydroxypivaldehyde to hydroxypivalyl hydroxypivalate, by the so called Tischenko reaction, is well known in the art. For example, magnesium ethyl iodide has been used to catalyze this reaction, as described by Franke and Kohn in Monatsheft Fur Chemie, Vol. 25, page 865 (1904).

Representative of more recent work in this area is U.S. Pat. No. 3,862,215 (1975) wherein the use of magnesium hydroxide and magnesium oxide are described as catalyst for the conversion of hydroxypivaldehyde to produce hydroxypivalyl hydroxypivalate. The oxide or hydroxide catalysts disclosed in this reference are used in the presence or absence of water at concentrations ranging from 0.1 up to 20 wt %, based on the weight of the total reaction mixture, with concentrations preferably falling in the range of 1 up to 5 wt %. Catalyst is then removed from the crude product by filtration prior to further product purification by distillation.

The difficulties encountered in removing magnesium hydroxide or magnesium oxide catalysts from hydroxypivalyl hydroxypivalate reaction product by filtration of the reaction mixture are described by Merger and Deumbgen in U.S. Pat. No. 3,852,335 (1974). This reference teaches that filtration to remove reaction catalysts is greatly improved by neutralization of the reaction mixture with formic acid, thereby avoiding the formation of a pasty filter cake having low permeability.

An alternate means of dealing with the filtration problem is described in U.S. Pat. No. 4,665,219 (1987), wherein the removal of catalyst from the hydroxypivalyl hydroxypivalate-containing reaction mixture is accomplished in two steps. Catalyst is first neutralized, and then the resulting salts are removed by liquid-liquid extraction. The removal of basic calcium, barium, strontium, lithium, magnesium, cobalt, nickel, lead, bismuth, lanthanum, cerium, and zinc hydroxides, oxides and hydrated oxides to levels as low as 0.02% are suggested.

The presence of residual reaction catalysts and/or neutralization salts thereof, can cause difficulties in the further purification of the hydroxypivalyl hydroxypivalate product, because such metal-containing materials can cause decomposition and disproportionation of the desired product at the temperatures encountered in purification by distillation (typically in the range of about 130° up to 200° C.). The presence of such residual reaction catalysts and/or neutralization salts thereof can also foul such processing equipment as distillation column base heat exchangers or the blades of wiped film evaporators.

Other catalysts known in the art to be useful for the conversion of hydroxy aldehydes to produce dihydroxy esters include metal alkoxides of aluminum, sodium, and titanium. See, for example, Journal of the American Chemical Society, Vol. 74, pages 5133-5135 (1952).

Accordingly, improved methods for the production and recovery of dihydroxy esters by the catalytic reaction of hydroxy aldehydes would be desirable.

STATEMENT OF THE INVENTION

In accordance with the present invention, there is provided a process for the preparation of dihydroxy esters from hydroxy aldehydes by contacting said hydroxy aldehydes with a small quantity of at least one of a selected group of catalytically active metals in elemental form.

The invention reaction does not require a catalyst neutralization step as part of the procedure for work-up of the reaction mixture. The very low levels of catalysts required for the invention reaction also minimize the potential for fouling of distillation equipment, as well as minimizing the potential for product decomposition during distillation.

DETAILED DESCRIPTION OF THE INVENTION

In accordance with the present invention, there is provided a process for the preparation of dihydroxy esters from hydroxy aldehydes, wherein said dihydroxy esters have the structural formula:

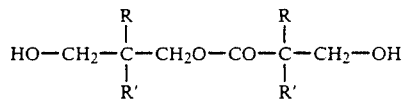

wherein each R and R' is independently a $C_1$ up to $C_4$ alkyl group, and wherein said hydroxy aldehydes have the structural formula:

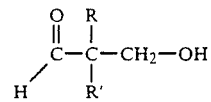

said process comprising:
contacting said hydroxy aldehyde with a catalytic amount of at least one catalytically active metal selected from:
elemental magnesium,
elemental zinc,
elemental manganese,
elemental aluminum,
elemental titanium, or
elemental calcium;
under conditions suitable to form said dihydroxy ester.

Hydroxy aldehydes contemplated for use in the practice of the present invention are compounds having the structural formula:

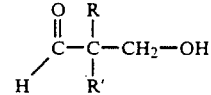

wherein R and R' are each independently a $C_1$ up to $C_4$ alkyl group. Presently preferred compounds are those wherein each of R and R' are methyl groups (i.e., hydroxypivaldehyde), or where each of R and R' are ethyl groups (i.e., 2,2-diethyl-3-hydroxyproponal), or where R is ethyl and R' is butyl (i.e., 2-butyl-2-ethyl-3-hydroxyproponal).

Catalysts contemplated for use in the practice of the present invention include
elemental magnesium, elemental zinc,
elemental manganese,
elemental aluminum,
elemental titanium,
elemental calcium,
and the like, as well as mixtures of any two or more thereof. The presently preferred catalytically active metal is elemental magnesium.

The quantity of catalytically active metal employed in the practice of the present invention can vary widely. Even very low levels of catalytically active metal will promote the invention process, although higher levels are usually desirable for further enhancement of the desired condensation reaction. Typically, at least 0.001 wt % of said at least one catalytically active metal, based on the weight of the total reaction mixture, will be employed for the practice of the present invention. Preferably, quantities in the range of about 0.005 up to 0.02 wt % of catalytically active metal will be employed in the practice of the present invention; with quantities in the range of about 0.007 up to 0.01 wt % of catalytically active metal being presently most preferred.

The invention reaction is relatively insensitive to reaction temperature and can be carried out over a wide range of temperatures. Typically, reaction temperatures in the range of about 50° up to 150° C. will be employed; with reaction temperatures in the range of about 80° up to 120° C. being presently preferred.

Reaction times contemplated for use in the practice of the present invention can also vary widely. Typically, reaction times fall in the range of about 0.5 up to 15 hours; with reaction times in the range of about 2 up to 8 hours being presently preferred.

The invention reaction is typically carried out neat, although added solvents can be employed if desired. When employed, solvents such as alcohols or esters are suitable for use in the practice of the present invention.

It is desirable that the amount of water in the reaction system be kept as low as possible, with water content in the reaction system typically being maintained below about 0.3 wt %. It is preferred that the contacting of hydroxy aldehyde with catalytically active metal be carried out under substantially water-free reaction conditions.

The invention will now be described in greater detail with reference to the following non-limiting examples.

EXAMPLE 1

This example is for comparison purposes. It describes the thermal reaction of dry hydroxypivaldehyde to hydroxypivalyl hydroxypivalate.

A crude mixture of hydroxypivaldehyde in water was prepared by the reaction of 1,440 grams (20 moles) of isobutyraldehyde and 910 grams (13.3 moles of 44 percent aqueous formaldehyde using 3 wt % sodium carbonate (70 grams). The mixture was stirred at 65° C. for 2 hours, washed with 2 aliquots of 1,000 mL distilled water and vacuum distilled at 100 mm Hg to a base temperature of 131° C. This gave a crude hydroxypivaldehyde feed that contained 0.1 wt % water and approximately 90 percent hydroxypivaldehyde. Other components included 2.5 percent neopentyl glycol monoisobutyrate (NPG MI), 3 percent neopentyl glycol (NPG) and 4.5 percent hydroxypivalyl hydroxypivalate.

A 200 gram aliquot of this feed was heated to 105° C. with stirring and periodically analyzed by gas chromatography for conversion of hydroxypivaldehyde to hydroxypivalyl hydroxypivalate. The hydroxypivaldehyde conversion was 85 percent after 17 hours. The crude product contained 78 percent hydroxypivalyl hydroxypivalate, 14 percent hydroxypivaldehyde, 3 percent NPG MI, 4 percent NPG, and 0.4 percent formate ester of hydroxypivalyl hydroxypivalate.

EXAMPLE 2

This example shows the effect of adding magnesium metal to dry hydroxypivaldehyde. A 200 gram aliquot of hydroxypivaldehyde prepared as described in Example 1 was treated with 0.02 grams (100 ppm) powdered magnesium (200 mesh). The mixture was heated to 90° C. with stirring. An exothermic reaction occurred which required external cooling to keep the temperature at 105° C. The hydroxypivaldehyde conversion was 90 percent after 2 hours.

The reaction mixture was pale grey. Analysis for soluble magnesium gave 80 ppm. The product was analyzed by gas chromatography to be 82.5 percent hydroxypivalyl hydroxypivalate, 10 percent hydroxypivaldehyde, 3.0 percent NPG MI, 3.5 percent NPG and 0.2 percent formate ester of hydroxypivalyl hydroxypivalate.

EXAMPLE 3

This example demonstrates the effect of adding Ca(OH)$_2$ at 100 and 1000 ppm. An aliquot of hydroxypivaldehyde prepared as described in Example 1 was treated with 0.02 grams (100 ppm) Ca(OH)$_2$ powder. The reaction mixture was heated to 105° C. with stirring. The hydroxypivaldehyde conversion was 55 percent after 2 hours and 70 percent after 5 hours. The reaction was repeated with 1,000 ppm Ca(OH)$_2$ (0.2 g). The reaction was exothermic and had to be cooled. The hydroxypivaldehyde conversion was 95 percent after 0.5 hours.

EXAMPLE 4

This example demonstrates the effect of adding a magnesium alkoxide to hydroxypivaldehyde feed. A 200 gram aliquot of hydroxypivaldehyde prepared as described in Example 1 was treated with 0.03 gram (150 ppm) of powdered magnesium ethoxide. The mixture was heated to 105° C. The hydroxypivaldehyde conversion was 57 percent after 2 hours.

EXAMPLE 5

This example demonstrates the effect of adding magnesium oxide to hydroxypivaldehyde feed. Powdered magnesium oxide 0.4 grams (2,000 ppm) was added to hydroxypivaldehyde prepared as described in Example 1. The hydroxypivaldehyde conversion was 90 percent after 2 hours. The reaction was repeated with 0.03 grams (150 ppm) magnesium oxide. The conversion was 45 percent after 4 hours and 85 percent after 15 hours.

EXAMPLE 6

This example demonstrates the continuous production of hydroxypivalyl hydroxypivalate. The feed contained 15 percent water, 10 percent NPG, 3 percent NPG MI, 70 percent hydroxypivaldehyde, and 2 percent hydroxypivalyl hydroxypivalate. A continuous system consisting of a drying column, 2-stage stirred tank reactor, flash column, and 2 vacuum distillation columns was used to prepare hydroxypivalyl hydroxypivalate using separately: (1) magnesium powder, (2)

magnesium oxide, and (3) calcium hydroxide, as catalyst.

The minimum catalyst loading that would provide an 80 to 90 percent hydroxypivaldehyde conversion at 105° C. and 4 hours residence time was determined. The amounts found to be required to satisfy these criteria were (1) 80 ppm magnesium powder, (2) 2,000 ppm MgO, and (3) 2,000 ppm Ca(OH)$_2$.

The attempted distillation of the Ca(OH)$_2$ containing crude hydroxypivalyl hydroxypivalate resulted in extensive polyester formation in the first column. Neutralization with acetic acid did not improve the yield to hydroxypivalyl hydroxypivalate which remained at 40 to 50 percent. Attempts to remove the Ca(OH)$_2$ or Ca(Ac)$_2$ by filtration resulted in rapid clogging of the filter as described in U.S. Pat. No. 3,852,335 (1974). The "pasty filter cake" formed very rapidly, stopping the filtrate flow.

Distillation of the magnesium powder generated crude hydroxypivalyl hydroxypivalate proceeded smoothly. Polyester formation was minimal (less than 5 percent) and a high quality hydroxypivalyl hydroxypivalate product could be obtained in 90 percent yield based on hydroxypivaldehyde consumed. The base of the high boiler removal column contained 1,600 ppm magnesium which was 95 percent of the magnesium added.

The invention has been described in detail with particular reference to preferred embodiments thereof, but it will be understood that variations and modifications can be effected within the spirit and scope of the invention.

We claim:

1. A process for the preparation of dihydroxy esters from hydroxy aldehydes, wherein said dihydroxy esters have the structural formula:

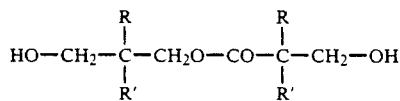

wherein each R and R' is independently a $C_1$ up to $C_4$ alkyl group, and wherein said hydroxy aldehydes have the structural formula:

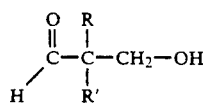

said process comprising:
contacting said hydroxy aldehyde with a catalytic amount of at least one catalytically active metal selected from:
elemental magnesium,
elemental zinc,
elemental manganese,
elemental aluminum,
elemental titanium, or
elemental calcium;
under conditions suitable to form said dihydroxy ester.

2. A process in accordance with claim 1 wherein at least 0.001 wt % of said at least one catalytically active metal is employed for said contacting.

3. A process in accordance with claim 1 wherein said conditions suitable to form said dihydroxy ester comprise a temperature in the range of about 50 up to 150° C. for a time in the range of about 0.5 up to 15 hours.

4. A process in accordance with claim 1 wherein said conditions suitable to form said dihydroxy ester comprise a temperature in the range of about 80° up to 120° C. for a time in the range of about 2 up to 8 hours.

5. A process in accordance with claim 1 wherein said contacting is carried out under substantially water free conditions.

6. A process in accordance with claim 1 wherein less than about 0.3 wt % water is present during said contacting.

7. A process in accordance with claim 1 wherein each R is ethyl and each R' is butyl.

8. A process in accordance with claim 1 wherein R=R'=methyl.

9. A process in accordance with claim 1 wherein R=R'=ethyl.

10. A process for the preparation of dihydroxy esters from hydroxy aldehydes, wherein said dihydroxy esters have the structural formula:

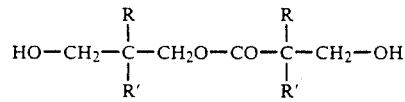

where each R and R' is independently a $C_1$ up to $C_4$ alkyl group, and wherein said hydroxy aldehydes have the structural formula:

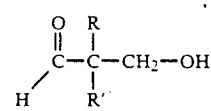

said process comprising:
contacting said hydroxy aldehyde with about 0.005 up to 0.02 weight percent of at least one catalytically active metal selected from:
elemental magnesium,
elemental zinc,
elemental manganese,
elemental aluminum,
elemental titanium, or
elemental calcium;
under conditions suitable to form said dihydroxy ester.

11. A process in accordance with claim 10 wherein said at least one catalytically active metal is present in a quantity falling in the range of about 0.007 up to 0.01 wt %.

12. A process for the preparation of dihydroxy esters from hydroxy aldehydes, wherein said dihydroxy esters have the structural formula:

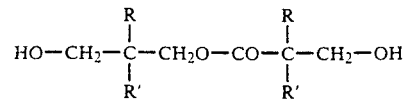

wherein each R and R' is indepently a $C_1$ up to $C_4$ alkyl group, and wherein said hydroxy aldehydes have the structural formula:

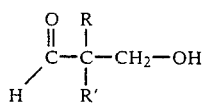
said process comprising:
contacting said hydroxy aldehyde with a catalytic amount of elemental magnesium, under conditions suitable to form said dihydroxy ester.
* * * * *